(12) United States Patent
Emanuel

(10) Patent No.: US 7,249,602 B1
(45) Date of Patent: Jul. 31, 2007

(54) SURGICAL ENDOSCOPIC CUTTING DEVICE AND METHOD FOR ITS USE

(75) Inventor: Mark Hans Emanuel, Bloemendaal (NL)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/486,977

(22) PCT Filed: Sep. 4, 1998

(86) PCT No.: PCT/NL98/00504

§ 371 (c)(1),
(2), (4) Date: Mar. 6, 2000

(87) PCT Pub. No.: WO99/11184

PCT Pub. Date: Mar. 11, 1999

(30) Foreign Application Priority Data

Sep. 4, 1997 (NL) .................................. 1006944

(51) Int. Cl.
*A61F 19/00* (2006.01)
*A61B 17/32* (2006.01)

(52) U.S. Cl. .................. 128/898; 606/170; 606/15

(58) Field of Classification Search .......... 606/1, 606/13–16, 14, 159, 170–185, 45, 46, 49, 606/50; 604/22; 128/898
See application file for complete search history.

(56) References Cited

U.S. PATENT DOCUMENTS

| 1,666,332 | A | | 4/1928 | Hirsch |
| 3,996,921 | A | | 12/1976 | Neuwirth |
| 4,449,538 | A | | 5/1984 | Corbitt et al. |
| 4,543,965 | A | | 10/1985 | Pack et al. |
| 4,756,309 | A | * | 7/1988 | Sachse et al. ................. 604/22 |
| 4,924,851 | A | | 5/1990 | Ognier et al. .................. 128/4 |
| 4,950,278 | A | * | 8/1990 | Sachse et al. ............... 606/170 |
| 4,955,882 | A | * | 9/1990 | Hakky et al. ................. 606/14 |
| 4,998,527 | A | | 3/1991 | Meyer |
| 4,998,914 | A | | 3/1991 | Wiest et al. |
| 5,037,386 | A | | 8/1991 | Marcus et al. |
| 5,163,433 | A | * | 11/1992 | Kagawa et al. ................. 601/2 |
| 5,195,541 | A | * | 3/1993 | Obenchain ................... 128/898 |
| 5,320,091 | A | | 6/1994 | Grossi et al. |
| 5,392,765 | A | | 2/1995 | Muller |
| 5,449,356 | A | * | 9/1995 | Walbrink et al. ............. 606/49 |
| 5,456,689 | A | * | 10/1995 | Kresch et al. ............. 606/180 |
| 5,492,537 | A | | 2/1996 | Vancaillie |
| 5,498,258 | A | | 3/1996 | Hakky et al. |
| 5,549,541 | A | | 8/1996 | Muller |
| 5,556,378 | A | | 9/1996 | Storz et al. |
| 5,569,254 | A | * | 10/1996 | Carlson et al. ............. 606/170 |
| 5,603,332 | A | | 2/1997 | O'Connor |
| 5,630,798 | A | | 5/1997 | Beiser et al. |

(Continued)

FOREIGN PATENT DOCUMENTS

DE 36 01 453 9/1986

(Continued)

*Primary Examiner*—Vy Q. Bui
(74) *Attorney, Agent, or Firm*—Fish & Richardson P.C.

(57) ABSTRACT

A surgical endoscopic cutting device includes cutting elements fitted in a protective tube. The device has an inlet for fluid, a discharge outlet for tissue and fluid, and a further outlet that discharges most of the fluid.

12 Claims, 3 Drawing Sheets

U.S. PATENT DOCUMENTS

| | | | |
|---|---|---|---|
| 5,695,448 A * | 12/1997 | Kimura et al. | 600/121 |
| 5,730,752 A * | 3/1998 | Alden et al. | 604/35 |
| 5,749,885 A | 5/1998 | Sjostrom et al. | |
| 5,749,889 A * | 5/1998 | Bacich et al. | 606/198 |
| 5,759,185 A * | 6/1998 | Grinberg | 606/80 |
| 5,772,634 A | 6/1998 | Atkinson | |
| 5,814,009 A | 9/1998 | Wheatman | |
| 5,840,060 A | 11/1998 | Beiser et al. | |
| 5,913,867 A | 6/1999 | Dion | |
| 5,944,668 A | 8/1999 | Vancaillie et al. | |
| 5,947,990 A | 9/1999 | Smith | |
| 5,956,130 A | 9/1999 | Vancaillie et al. | |
| 6,032,673 A | 3/2000 | Savage et al. | |
| 6,086,542 A | 7/2000 | Glowa et al. | |
| 6,090,123 A | 7/2000 | Culp et al. | |
| 6,113,594 A * | 9/2000 | Savage | 128/898 |
| 6,156,049 A * | 12/2000 | Lovato et al. | 606/170 |
| 6,159,160 A | 12/2000 | Hsei et al. | |
| 6,159,209 A * | 12/2000 | Hakky | 606/45 |
| 6,626,827 B1 | 9/2003 | Felix et al. | |

FOREIGN PATENT DOCUMENTS

| | | |
|---|---|---|
| DE | 196 33 124 | 5/1997 |
| EP | 0 327 410 | 8/1989 |
| EP | 0327410 B1 | 8/1989 |
| EP | 0 557 044 | 8/1993 |
| GB | 2 093 353 | 9/1982 |
| WO | WO 93/07821 | 4/1993 |
| WO | WO 93/15664 | 8/1993 |
| WO | WO 95/30377 | 11/1995 |
| WO | WO 96/11638 | 4/1996 |

* cited by examiner

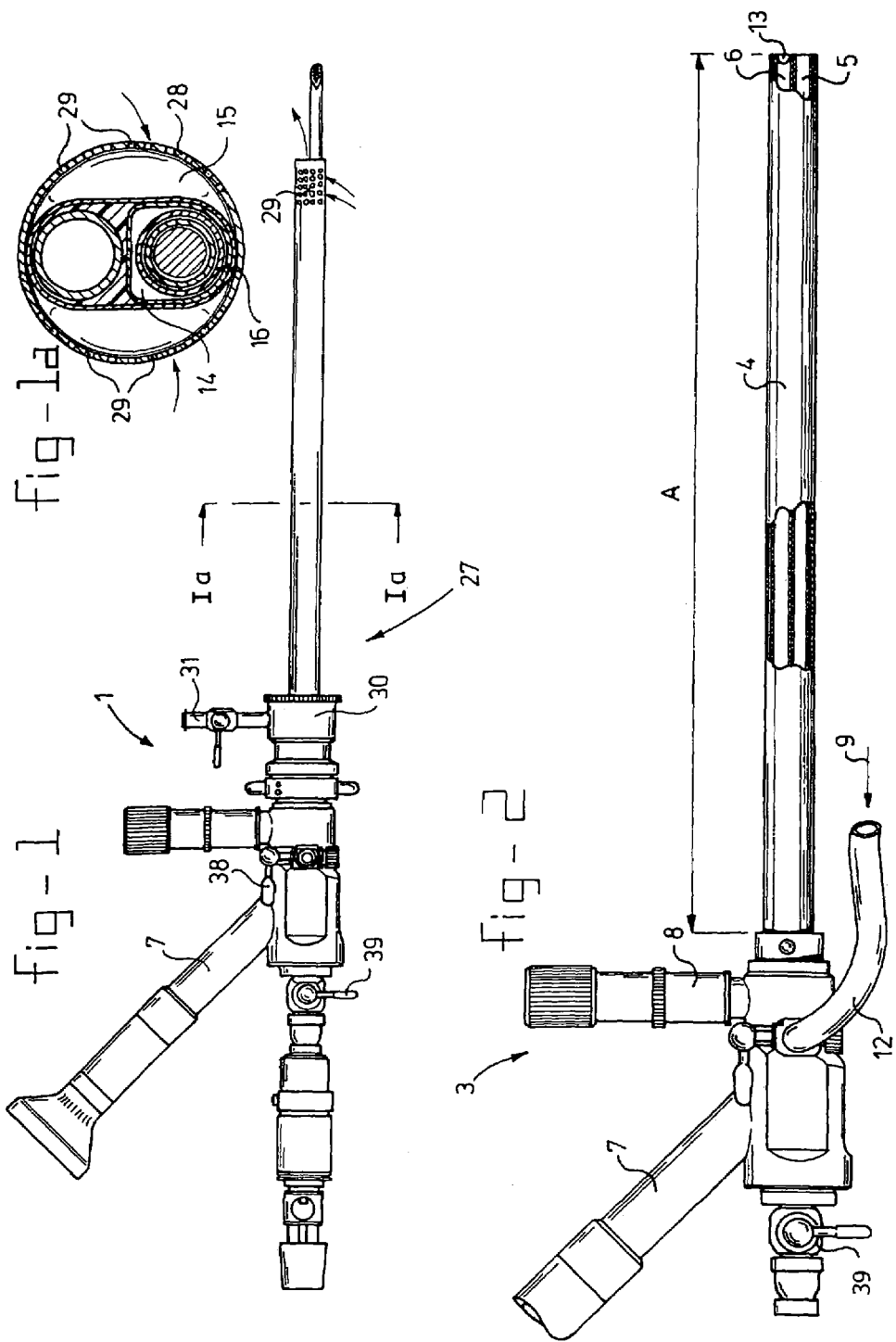

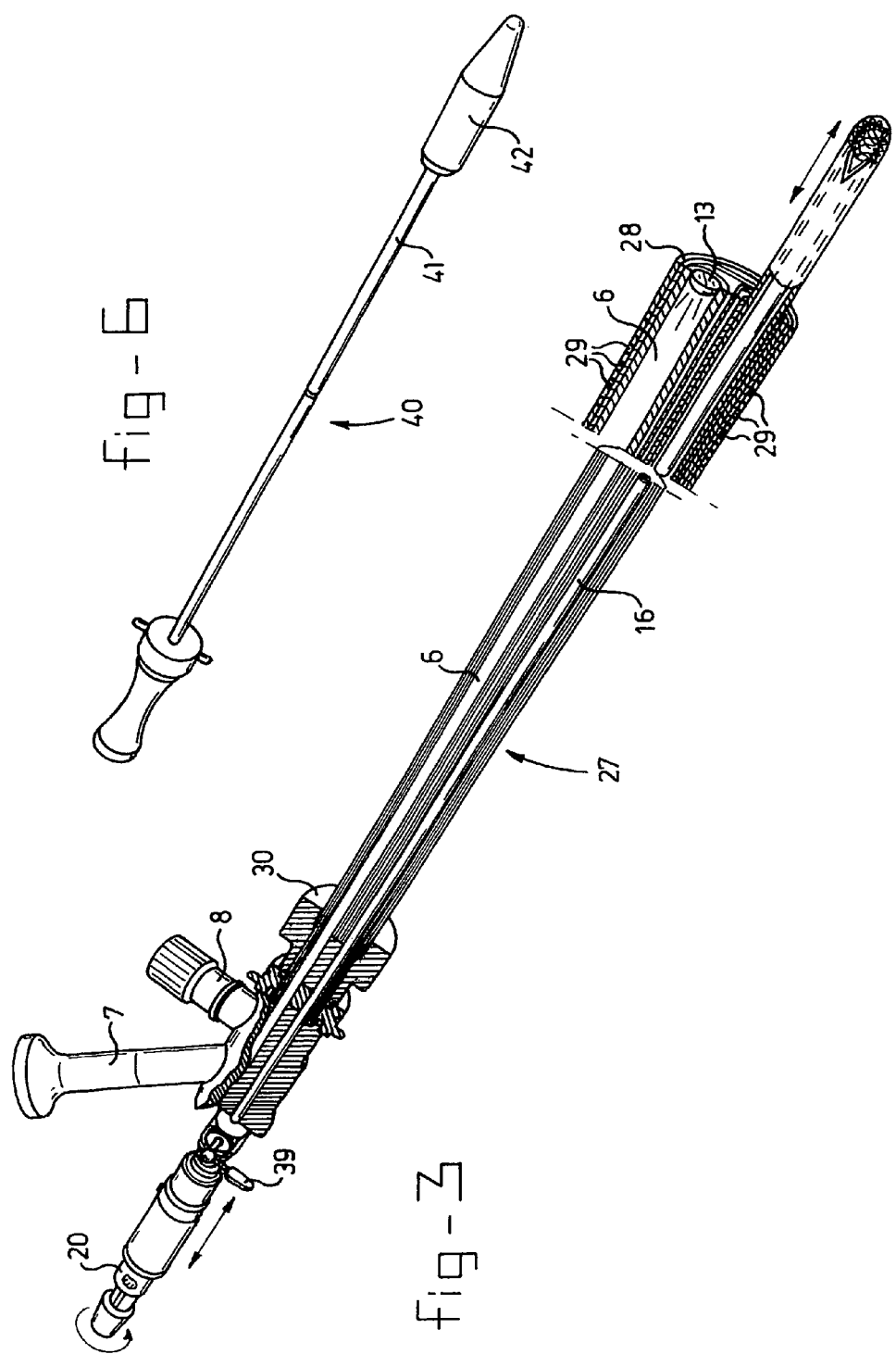

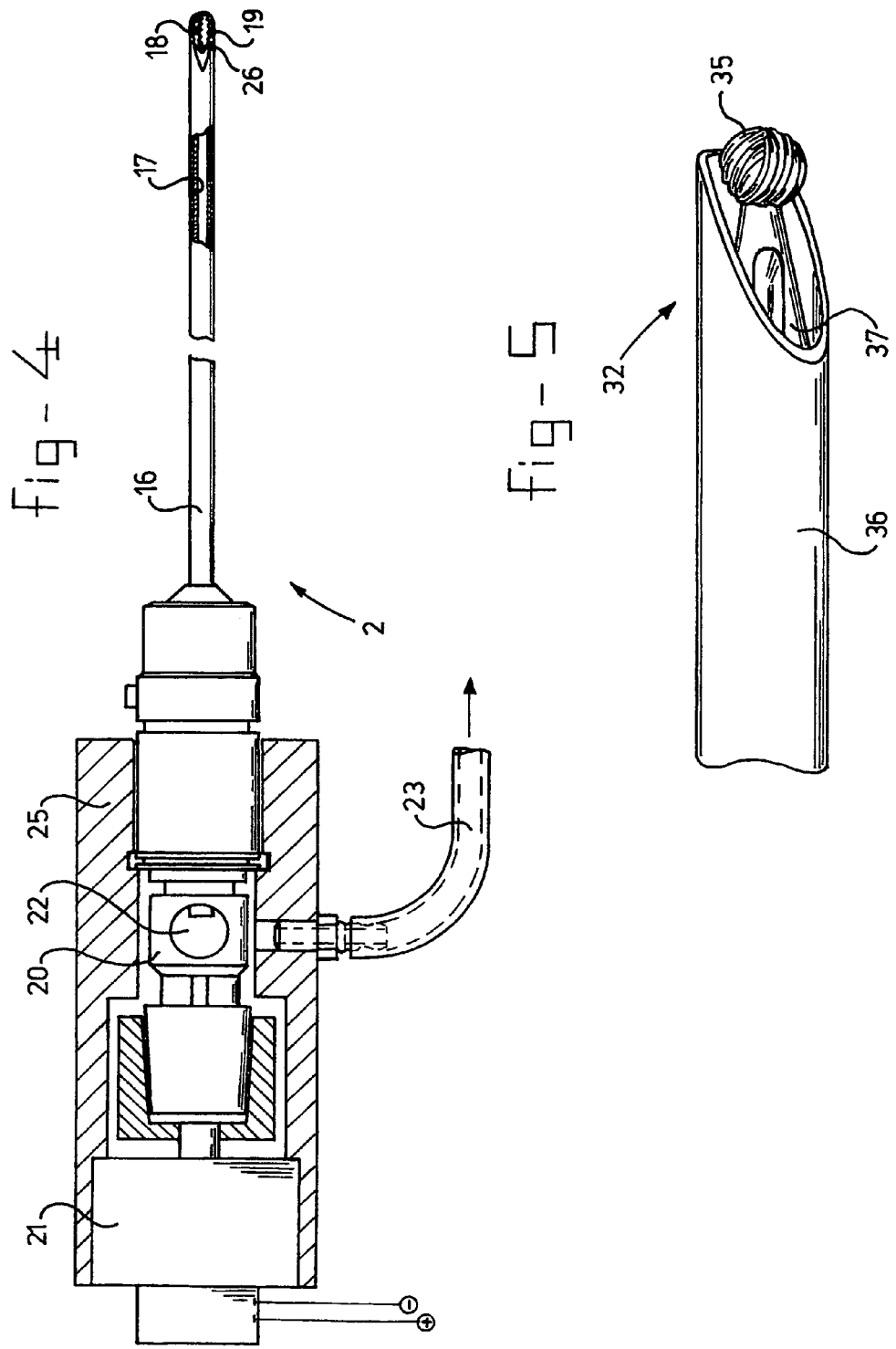

SURGICAL ENDOSCOPIC CUTTING DEVICE AND METHOD FOR ITS USE

FIELD OF THE INVENTION

The present invention relates to a surgical endoscopic cutting device.

BACKGROUND OF THE INVENTION

Surgical cutting devices are generally known and used for the removal of hard and/or soft tissue, such as in the vicinity of the knee joint. Such cutting devices are used in, for example, a joint cavity, where they can be guided endoscopically by separately inserting a viewing device having a light source and an observation portion. Such operations are successfully used in organs and joints lying not too deep underneath the skin.

When operations are being carried out on organs lying deeper, other techniques are currently used. If, for example, tissue has to be removed from the uterus, prostate, or urinary bladder, such as mucous membrane or other tissues, it was customary until now to use a so-called "loop." This is a loop-shaped cutting wire which is brought to a first potential, while the wall of the uterus is brought to a second, different potential. Tissue is removed by moving the loop along the uterus wall. In order to be able to carry out such an operation, it is necessary to dilate the uterus. Dilation is carried out by introducing a fluid. In order to maintain the effect of the potential difference, a non-conducting fluid is used, for example a 5% sorbitol solution. Because wounds are caused during the treatment described above, a good part of this fluid is resorbed into the patient's bloodstream (by way of the uterus). This can lead to highly dangerous electrolyte displacements. It has been found that the tissue can be removed more easily by working with a high-frequency monopolar electric current, but there is a risk of high-frequency electric current leading to internal and external burns. The loop is generally fitted on an endoscope and moved back and forth along the uterus wall with the endoscope. The tissue cut off during this treatment has to be removed from the uterus, which considerably extends the duration of the operation. Furthermore, the doctor has to check that all detached material actually has been removed.

This means that such operations are very time-consuming and require the surgeon to repeatedly move the device back and forth. This is tiring and consequently difficult to learn. Moreover, the patient has to be monitored continually during the operation, in order to prevent the undesirable phenomena described above. It is not uncommon for such an operation to be broken off because the patient's life is endangered by the side effects.

On the other hand, it is desirable to be able to carry out such operations instead of simply performing a hysterectomy.

WO 96/11638 discloses a cutter including a hollow stem and a cutting head accommodated inside a rigid housing. This rigid housing likewise contains a viewing channel with the necessary optics. U.S. Pat. No. 5,195,541 describes a laproscopic discectomy apparatus. For a laproscopic method it is essential to inflate the related cavity using gas. The gas feed is discontinuous and has no effect on viewing of the operation site.

Fluid is introduced by way of a space between the stem and the rigid housing and discharged together with the detached tissue through the hollow stem of the cutter.

This device could be satisfactory for the removal of tissues from certain body cavities, such as from the bladder. However, in the case of other body cavities, it is necessary to "blow up" the cavity before treatment can be carried out. An example of this is the uterus, in which it is important that the amount of enlargement of the organ be accurately controlled. The irregular discharge of fluid through the hollow stem of the cutter, caused partly by the irregular release of tissue, means that it cannot be guaranteed that the pressure inside the cavity is accurately controlled.

Such a device is consequently not very suitable for use in the treatment of such a cavity.

SUMMARY OF THE INVENTION

The object of the present invention is to provide a device which can perform such a treatment.

According to the invention, a further outlet channel is provided, the function of which is independent of whether or not detached tissue has been released. In other words, a regular discharge of fluid can occur through this further outlet channel. Since only a minor part of the fluid is now discharged through the outlet, in which there are detached pieces of tissue, the pressure inside the body cavity can be regulated and controlled accurately. This makes it possible to remove undesired tissue from cavities such as the uterus. The applicability of the removal of tissues by cutting is consequently considerably increased.

The further outlet channel described above is formed by an insertion tube fitted around the endoscopic device. This insertion tube serves to clear a space for the endoscopic device. For this purpose, the front side of the insertion tube can be provided with an insertion mandrel, which is removed after the positioning of the insertion tube and replaced by the endoscopic device described above. In this case the further outlet channel can be defined between the endoscopic device and the insertion tube.

In the case of such a construction it is desirable for a coupler to be present to provide a coupling between the rigid housing and the insertion tube described above.

Discharge of the tissue material which has been detached can be achieved either by making the stem on which the cutting elements are fitted hollow, or by fitting a protective tube around the cutter. Such a protective tube can also be used without the space between protective tube and stem serving as an outlet channel. This means that the cutter can be designed as a separate unit which can be coupled to the rigid housing, which has advantages in particular for purposes of sterilization. Namely, the device can then be detached in a simple way.

For the removal of tissue from a uterus it is essential for the rigid housing to have a length which is sufficient to reach all tissue parts, i.e. a length of at least 30 cm.

The observation part of the device described above includes a light channel in the housing, provided near one end with a lens and near the other end with an observation mechanism. The latter can include an eyepiece or a connection for a camera so that the surgeon can carry out the operation using a monitor and others can possibly look at the same time.

The cutting elements described above can include any cutting element known in the prior art. In other words, a cutting head with cutting faces can be used, but it is also possible to use constructions with teeth, meshing with the protective tube or otherwise. In the latter instance, the protective tube is preferably provided with a lateral opening through which a part of the cutting elements extends so that on each revolution, part of the tissue is removed and can be discharged directly through the interior of the drive/discharge tube of the cutter.

The invention also relates to a method for the removal of uterus tissue in which the device described above is used. In other words, a machining operation is now applied with the use of a physiological fluid which can be electrically conducting without any problem, while at the same time the removed tissue is sucked out. It is, of course, possible to suck out the tissue at a later stage. The machining operation is carried out by a rotating action.

According to a further embodiment of the method, an outlet and a further outlet are present, and the pressure inside the body cavity is regulated by metering the quantity of fluid which moves through the further outlet. The insertion of the surgical endoscopic cutting device is preferably carried out in the manner described above using an insertion mandrel and insertion tube.

BRIEF DESCRIPTION OF THE DRAWINGS

The invention will be explained in greater detail below with reference to an exemplary embodiment shown in the drawings, in which:

FIG. 1 shows the endoscopic cutting device according to the invention in the assembled state, in side view and partially in section;

FIG. 1a shows the viewing/receiving part of the cutting device of FIG. 1 in section along the line Ia-Ia;

FIG. 2 shows a side and partially cut-away view of the viewing/receiving part of the cutting device of FIG. 1;

FIG. 3 shows a partially cut-away perspective view of the device of FIG. 1, with the insertion end enlarged;

FIG. 4 shows a partially sectional side view of the cutter of the cutting device of FIG. 3;

FIG. 5 shows a variant of the cutter shown in FIG. 4; and

FIG. 6 shows an insertion mandrel according to the invention.

DETAILED DESCRIPTION

The endoscopic cutting device according to the invention is indicated in its entirety by 1 in FIG. 1. It comprises a viewing/receiving part 3, which is shown in FIG. 2, a cutting part 2, which is shown in greater detail in FIGS. 4 and 5, and an insertion mandrel, which is shown in FIG. 6.

With reference to FIG. 2, it can be seen that the viewing/receiving part 3, is composed of an outer tube 4 in which a main channel 5 and viewing channel 6 are defined. Viewing channel 6 ends at one side in a lens 13 and at the other side in a viewing tube 7, on which an eyepiece or camera connection is placed. A connection 8 for a light source is also present, for connection to a fibre optics bundle which provides for lighting at the end of lens 13. Near the control end, tube 4 is provided with a fluid inlet 9 connected to a hose 12, for adding a physiological salt solution.

A shut-off valve is indicated by 39.

The length of the actual outer tube 4, is indicated by A and is more than 30 cm.

FIG. 4 shows details of the cutter or the cutting part 2, which is composed of a protective tube 16 inside of which a drive/suction tube 17 is fitted. Near the working end, tube 17 is provided with teeth 19 which mesh with teeth 18 provided in an opening 26 in the end part of protective tube 16. Near the other end, drive/suction tube 17 is provided with a coupling 20, which can be connected at one end to a rotating drive motor 21, not shown in detail, and at the other end is provided with an opening 22 through which fluid and removed material can be discharged by way of suction tube 17 to the discharge hose 23. A pressure regulator can be present in this discharge hose 23, which is connected to a vacuum source.

In FIG. 1 the insertion part is indicated by 27. This insertion part is composed of an insertion tube 28 which is provided with openings 29 at one end and near the other end, the insertion part 27 is provided with a bayonet connection 30 and an outlet 31. Insertion tube 28 is designed in such a way that tube 4 can be fitted therein, as shown in FIGS. 1 and 3, while it is also possible to fit insertion mandrel 40, provided with stem 41 and mandrel 42, in insertion tube 28.

The construction described above has an inlet 38 for fluid. Inlet 38 extends to channel 14 (FIG. 1a), i.e. the space bounded between the outer tube 4 and the protective tube 16 and 36, respectively from FIG. 4 or 5. A shut-off valve 39, which is connected to channel 14, is present, while the further outlet is indicated by 31. A discharge hose 23 for tissue and fluid is shown. During the removal of tissue, with a substantially continuous supply of fluid through inlet 38, some of the fluid will be discharged through outlet 23. This relatively small amount will be mixed with a mixture released during the cutting operation. Most of the fluid will be discharged through the further outlet 31. This discharge is unimpeded and occurs through openings 29. Pressure variations occurring due to the presence or absence of removed tissue in channel 17 (FIG. 4) have little or no influence on the pressure inside the body cavity owing to the presence of the further outlet 31.

If the device is to be inserted into, for example, a uterus, insertion mandrel 40 will first be inserted, with shut-off valve 39 open, into insertion tube 28 with bayonet 30. This assembly is then placed in the uterus in a relatively simple manner due to the shape of mandrel 42. Mandrel 42 is then removed by manipulating stem 41, and the construction shown in FIG. 2 is placed in tube 28. Connection is made here to bayonet 30. The cutting action can then begin after the uterus has been dilated by the introduction of fluid. This fluid can be a physiological flushing and distension fluid, such as a physiological salt solution (NaCl 0.9%). In the event of the (unavoidable) resorption of the physiological fluid into the blood, electrolyte displacement, with fatal consequences for the patient, will not occur. Owing to the absence of electrical current, the burns described above are also ruled out.

By switching on motor 21, tube 17 is set in rotation and teeth 19 move regularly along cutting edge 18 of protective tube 16 which remains stationary. While they are moving along each other and picking up tissue material between them, a cutting, detaching action on the tissue material is occurring. The cut, detached material is removed through the interior of tube 17 and outlet 23.

The appropriate area of the uterus can be treated by moving parts 18 and 19 along the uterus wall or along tissue to be removed, which can be observed through viewing tube 7 by supplying light through connection 8.

Through the use of a continuous flow system, a constantly clear view is obtained for the observer even if blood and/or mucous is/are in the mixture. Moreover, the pressure can be maintained as low as possible, in order to prevent intravasation.

FIG. 5 shows a variant of the end of the cutter. The cutter or cutting part are indicated in their entirety by 32. The protective tube is indicated by 36 and is bevelled near the end. The drive/suction tube is indicated by 37 and provided with a cutting head near the end. In this embodiment, there is either no interaction between cutting head 35 and protective tube 36, or head 35 and tube 36 interact near the edge of tube 36, which is adapted for that purpose by grinding.

It is understood that such cutting elements can be designed in any way known in the prior art.

These and further modifications are considered to lie within the scope of the present application, to be immediately obvious to the person skilled in the art after reading the description, and to lie within the scope of the appended claims. For instance, it is possible to effect the supply of working fluid and the discharge of cleaning material in another way, i.e., to arrange the interior of housing 4 slightly differently. Furthermore, the method described above can be used for the removal of other tissue material, such as prostate tissue through the urethra, or for the removal of tissue from the wall of the urinary bladder.

The invention claimed is:

1. Method for the removal of tissue from a distensible organ, comprising
    inserting into said distensible organ a device for cutting and detaching said tissue,
    introducing a fluid into said distensible organ,
    discharging fluid with detached tissue along a first path, and
    discharging substantially only fluid along a second path, said discharge along said second path being regulated by metering the quantity of fluid which moves through the second path to control pressure in said distensible organ.

2. Method according to claim 1, in which the pressure in said distensible organ is substantially constant.

3. Method according to claim 2, in which inserting the device into said distensible organ comprises
    inserting an insertion mandrel, and
    removing the insertion mandrel prior to inserting the device.

4. Method according to claim 1, in which inserting the device in to said distensible organ comprises
    inserting an insertion mandrel, and
    removing the insertion mandrel prior to inserting the device.

5. The method of claim 1 wherein the motor comprises a rotating motor.

6. The method of claim 1 wherein inserting the device into the cavity comprises inserting the device through a valve of an endoscope.

7. The method of claim 1 wherein the first path is completely separate from the second path.

8. The method of claim 1 wherein introducing fluid into said distensible organ includes introducing fluid into said distensible organ to enlarge said distensible organ.

9. Method for the removal of tissue from a body cavity, comprising
    inserting a device into said cavity for cutting and detaching said tissue,
    introducing a fluid into said cavity,
    discharging fluid with detached tissue along a first path terminating at a first path source of suction, and
    discharging substantially only fluid along a second path terminating at a second path source of suction, said second path being completely separate from said first path,
    wherein said discharge along said second path is regulated by metering the quantity of fluid which moves through the second path to control pressure in said body cavity.

10. The method of claim 9 wherein inserting the device into the cavity comprises inserting the device through a valve of an endoscope.

11. The method of claim 9 wherein the first path source of suction is a different source from the second path source of suction.

12. Method for the removal of tissue from a body cavity, comprising
    inserting into said cavity a device having at least one of a sharp edge and teeth for cutting and detaching said tissue,
    introducing a fluid into said cavity,
    discharging fluid with detached tissue along a first path, and
    discharging substantially only fluid along a second path, said discharge along said second path being regulated by metering the quantity of fluid which moves through the second path to control pressure in said body cavity.

* * * * *